United States Patent [19]

Anderson

[11] Plant 4,791

[45] Nov. 17, 1981

[54] NECTARINE TREE

[76] Inventor: Frederic W. Anderson, 826 W. 22nd St., Merced, Calif. 95340

[21] Appl. No.: 187,850

[22] Filed: Sep. 15, 1980

[51] Int. Cl.[3] ..... A01H 5/03
[52] U.S. Cl. ..... Plt./41
[58] Field of Search ..... Plt./41

*Primary Examiner*—Robert E. Bagwill
*Attorney, Agent, or Firm*—Roger B. Webster

[57] ABSTRACT

A nectarine tree which is large, spreading, vase formed; foliated with medium size, lanceolate, acutely pointed leaves having a crenate margin and medium size, reniform glands; blooms medium season from hardy, medium size buds, the flowers being large and pink; and is a regular and productive bearer of large, uniform, symmetrical, globose-oblong, early-season, freestone fruit having yellow skin substantially entirely overspread with red when the fruit is fully ripe, and the flesh being yellow.

1 Drawing Figure

CLASSIFICATION OF THE VARIETY

The present variety of nectarine tree is embraced by Class 41, Plants, of the U.S. Patent Office Manual of Classification.

BACKGROUND OF THE VARIETY

1. Field of the Invention

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

2. Prior Varieties

Among the existent varieties of nectarine tree which are known to me, I make particular reference to Early Sun Grand (U.S. Plant Pat. No. 1,420), May Grand (U.S. Plant Pat. No. 2,794), and Red Diamond (U.S. Plant Pat. No. 3,165) as mentioned hereinafter in this specification.

Origin of the variety: The present variety of nectarine tree was originated by me as a cross between the Red Diamond nectarine and the Early Sun Grand nectarine; the variety, as so originated, having been grown under careful and continuing observation, and — upon evidencing desirable characteristics for commercial production — the variety was selected for asexual reproduction.

Asexual reproduction of the variety: Subsequent to origination and selection by me of the present variety of nectarine tree, I asexually reproduced it by top-working on orchard trees, and — in maturity — such reproductions ran true to the original tree in all respects.

Summary of the variety: The present variety of nectarine tree is large, spreading, vase formed; foliated with medium size, lanceolate, acutely pointed leaves having a crenate margin and medium size, reniform glands; blooms medium season from hardy, medium size buds, the flowers being large and pink; and is a regular and productive bearer of large, uniform, symmetrical, globose-oblong, early-season, freestone fruit having yellow skin substantially entirely overspread with red when the fruit is fully ripe, and the flesh being yellow.

The present variety of nectarine tree is further characterized by fruit which ripens two to three days after the May Grand nectarine and five to seven days before the Early Sun Grand nectarine — thus providing a nectarine harvest and market availability intermediate such other varieties.

The present variety of nectarine tree is still further characterized by fruit which is slightly larger, in average size, than the fruit of the May Grand nectarine and Early Sun Grand nectarine, and somewhat firmer than the latter.

BRIEF DESCRIPTION OF THE DRAWING

The drawing is an illustration, by photographic reproduction in color, of a twig with leaves, separate fruit, and a separate stone of the variety; one fruit being partially cut away to expose the flesh.

DESCRIPTION OF THE VARIETY

The botanical details of this new and distinct variety of nectarine tree — with color definitions (except those in common color terms) referenced to Maerz and Paul Dictionary of Color — are as follows:

Tree:
- *Size.*—Large.
- *Vigor.*—Vigorous.
- *Growth.*—Spreading.
- *Form.*—Vase-formed.
- *Production.*—Productive.
- *Bearing.*—Regular bearer.

Trunk:
- *Size.*—Medium.

Branches:
- *Size.*—Medium.

Leaves:
- *Size.*—Medium — large. Average length — 6". Average width — $1\frac{3}{8}$".
- *Form.*—Lanceolate. Acutely pointed.
- *Thickness.*—Medium.
- *Texture.*—Smooth.
- *Color.*—Top side — Medium green (23-L-8). Under side — Lighter green (22-K-6).
- *Margin.*—Crenate.
- *Petiole.*—Medium length — average $\frac{1}{2}$".
- *Glands.*—Average number — 2. Medium size. Reniform. Position — usually 2 or 3 on petiole and 1–3 on blade.

Flower buds:
*Hardiness.*—Hardy.
*Size.*—Medium.
Flowers:
*Blooming period.*—Medium, as compared with other varieties.
*Size.*—Large.
*Color.*—Pink.
Fruit:
*Maturity when described.*—Eating ripe — June 20, 1980.
*Date of first picking.*—June 10, 1980.
*Date of last picking.*—June 20, 1980.
*Size.*—Uniform. Large. Average diameter axially — $2\frac{3}{8}''$. Average transversely in suture plane — $2\frac{1}{4}''$.
*Form.*—Uniform. Symmetrical. Globose — oblong.
*Suture.*—Distinct.
*Base.*—Rounded.
*Apex.*—Short.
Skin:
*Thickness.*—Medium.
*Texture.*—Medium.
*Color.*—Yellow (10-L-4) substantially entirely overspread, when fully ripe, with red (5-L-4) shading to darker red (8-L-6).
Flesh:
*Color.*—Yellow (9-L-5).
*Juice.*—Abundant.
*Texture.*—Firm. Crisp.
*Fibers.*—Few.
*Ripens.*—Evenly.
*Flavor.*—Subacid to mild.
*Aroma.*—Wanting.

*Eating quality.*—Good to best.
Stone:
*Type.*—Free.
*Size.*—Medium. Average length — $1\frac{1}{4}''$. Average breadth — $1''$. Average thickness — $\frac{3}{4}''$.
*Form.*—Oblong.
*Base.*—Straight.
*Apex.*—Rounded.
*Sides.*—Equal.
*Pits.*—Elongated.
*Ventral edge.*—Thick.
*Dorsal edge.*—Shallow.
*Tendency to split.*—None noted.
*Color.*—Tan (12-J-8).
Use: Market. Long distance shipping.
Keeping quality: Good.
Resistance to insects and diseases: No unusual susceptibilities noted.
Shipping quality: Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, which is particularly characterized by the regular and productive bearing of yellow-flesh, freestone fruit which ripens intermediate the May Grand nectarine and the Early Sun Grand nectarine; the fruit being of slightly larger average size in comparison to said May Grand nectarine and Early Sun Grand nectarine, and somewhat firmer than the latter.

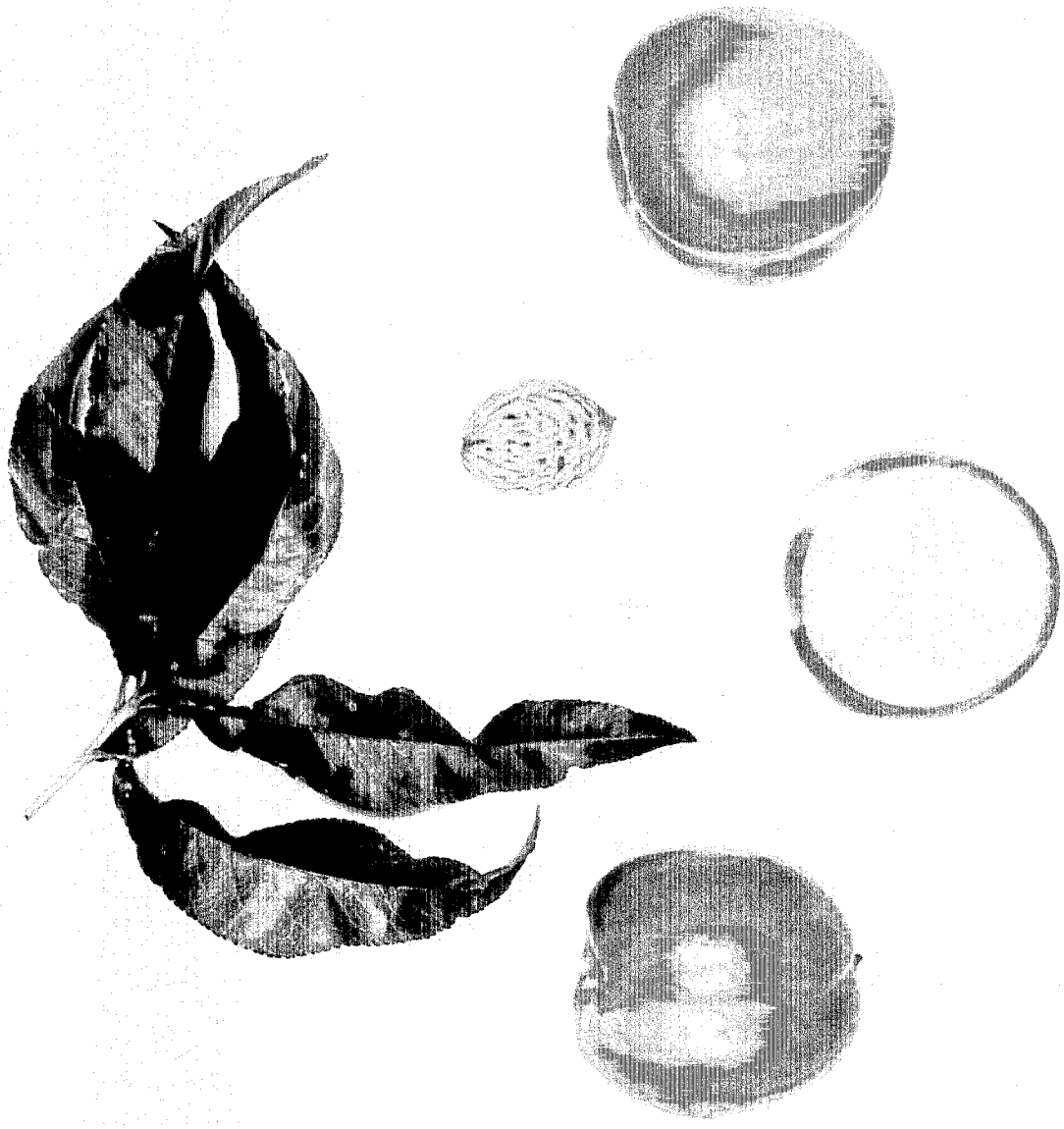

* * * * *